United States Patent [19]

Ogden

[11] Patent Number: 4,478,666

[45] Date of Patent: Oct. 23, 1984

[54] MEMBRANE SWITCH CONTROL PANEL ARRANGEMENT AND LABEL ASSEMBLY FOR LABELING SAME

[76] Inventor: Ralph Ogden, 1304 Fisher St., Munster, Ind. 46321

[21] Appl. No.: 426,068

[22] Filed: Sep. 28, 1982

Related U.S. Application Data

[62] Division of Ser. No. 317,594, Nov. 2, 1981, Pat. No. 4,387,127, which is a division of Ser. No. 148,907, May 12, 1980, Pat. No. 4,347,416.

[51] Int. Cl.³ .......................... B44C 1/16; B32B 31/00; H01H 9/00; A61F 13/02

[52] U.S. Cl. .................................. 156/240; 156/249; 156/292; 156/344; 156/277; 200/317; 428/42; 428/914

[58] Field of Search .................... 200/5 R, 5 A, 159 B, 200/159 R, 310, 311, 312, 313, 317, 314, 308, 309; 428/40, 42, 41, 52, 202, 63, 914; 156/292, 277, 108; 40/360, 594; 116/DIG. 3

[56] References Cited

U.S. PATENT DOCUMENTS

| | | | |
|---|---|---|---|
| 3,591,749 | 7/1971 | Comstock | 200/308 |
| 3,811,025 | 5/1974 | Bach | 200/317 |
| 3,992,236 | 11/1976 | Wanesky | 156/344 |
| 4,028,474 | 6/1977 | Martin | 156/240 |
| 4,056,699 | 11/1977 | Jordan | 200/5 A |

*Primary Examiner*—Edward C. Kimlin
*Assistant Examiner*—Louis Falasco
*Attorney, Agent, or Firm*—McWilliams, Mann, Zummer and Sweeney

[57] ABSTRACT

A membrane switch control panel arrangement and a label assembly for labeling same, for providing for in field applied identification of the control panel legend upon assembly of the switch, in which the control panel arrangement is of the keyboard switch type providing for touch sensitive switch actuation, with the control panel arrangement circuit board circuiting, membrane or touch sensitive switch components therefor, and the control panel legend sheet switch location indicia therefor being arranged in superposed modular group form, and columnarily arranged, spaced apart switch actuation and observation sets, which sets are disposed in spaced apart rows and extending crosswise of the panel in a columnar configuration, with the legend sheet being delineated to receive and have adhered thereto individual in field marked labels that are to bear the switch identification indicia of the adjacent switch location indicia row. The label assembly comprises a carrier sheet and an adhesive backed label forming sheet that are both specially segmented to define specially shaped sections cooperation to remain united for application thereto, by using a typewriter or the like, the switch identification indicia involved that becomes known only when the assembly of the switch components and controls has been completed. The individual labels are shaped to be then expeditiously separated from the carrier sheet and centered on the respective legend blank spaces by way of throw-away end tab section arrangement that is part of the label assembly arrangement.

2 Claims, 12 Drawing Figures

FIG-1-
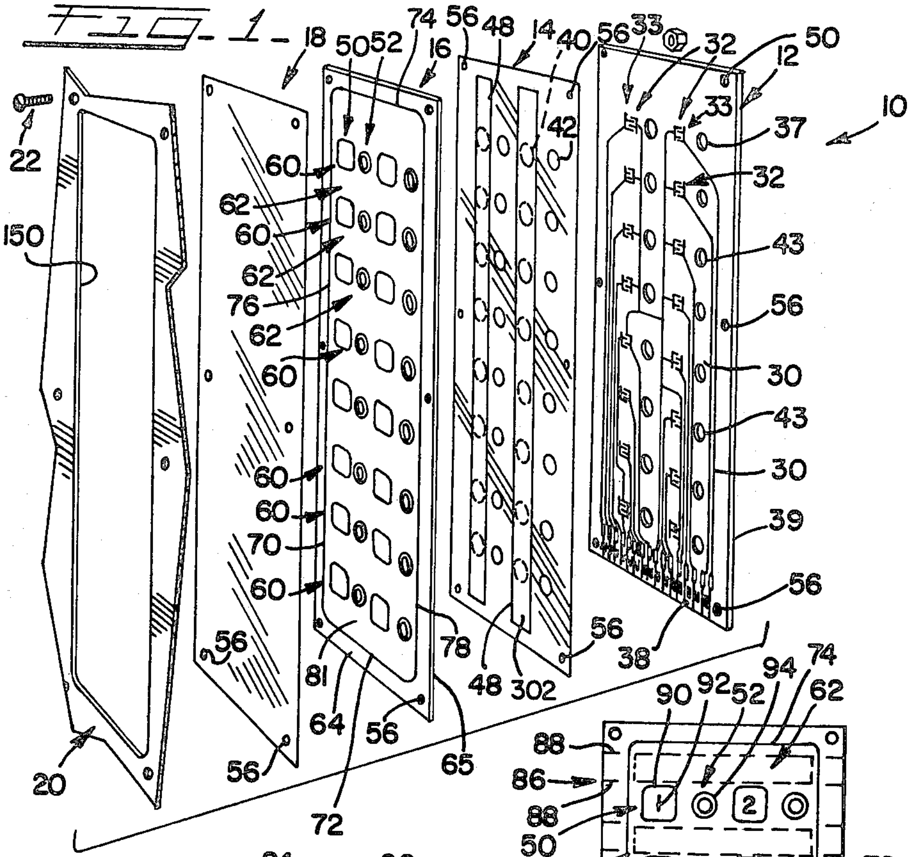
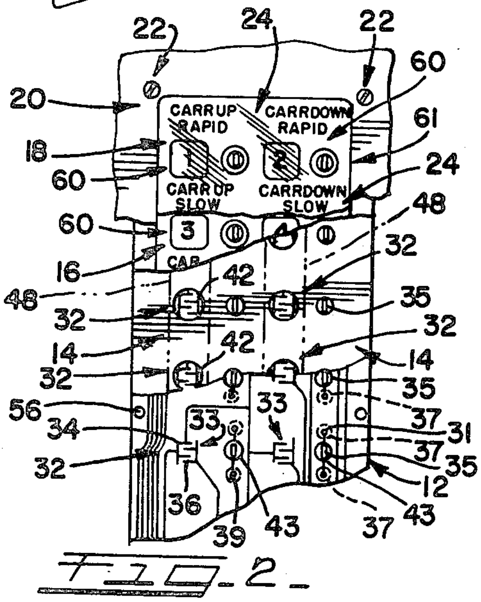
FIG-2-
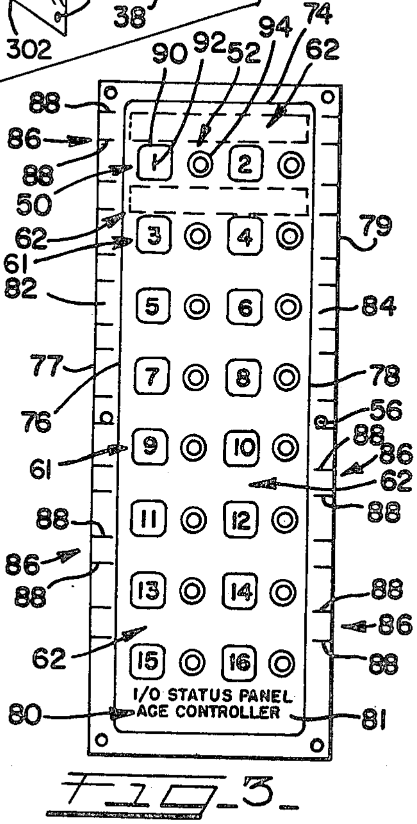
FIG-3-

MEMBRANE SWITCH CONTROL PANEL ARRANGEMENT AND LABEL ASSEMBLY FOR LABELING SAME

This application is a division of my application Ser. No. 317,594, filed Nov. 2, 1981, now U.S. Pat. No. 4,387,127 which is a division of my application Ser. No. 148,907, filed May 12, 1980, now U.S. Pat. No. 4,347,416, granted Aug. 31, 1982.

This invention relates to a membrane or keyboard switch control panel arrangement and label assembly therefor, and more particularly, to a legend arrangement for use in control panels of the membrane or keyboard switch type that are commonly employed in connection with programmable controllers.

Programmable controllers have come into common use in recent years as a manner of expeditiously controlling the operation of industrial processing equipment without having to use traditional electro-mechanical relay logic circuitry that was commonly used in older forms of industrial process control systems.

A typical programmable controller consists of one or more input modules, one or more output modules, one or more memory modules, and a processor, usually referred to as the central processing unit. The input module converts the status condition of the process variables into electrical signals that can be understood by the programmable controller. The output module converts the commands issued by the central processing unit into signals that can actuate or deactuate corresponding machine devices. It usually consists of solid state switches operated through the output interface to control power to the desired external devices. The memory module contains the instructions that represent the systems control circuitry and the action that is to be taken in response to each condition of the input devices. The central processing unit supervises the other sections of the system. The processor is conventionally operated from a suitable control panel, and it is the arrangement of the control panel to which this invention is directed.

It is common practice in this field to provide the programmable controller control panel with some means of identifying the components controlled thereby, that are ordinarily switch controls. As the correlation between a particular assembly of controlling switches and the functioning of the individual switches that is to be performed is not ordinarily possible in equipment of this type until an installation is completed, pre-labeling or pre-marking of the control panel legend is not possible. Thus in field marking or labeling of the control panel to provide some sort of workable legend therefor has been the practice followed. This practice has taken the form of individual strips of plastic each engraved with the needed identification indicia and fixed to the panel housing, using a suitable adhesive, adjacent the location of the switch control and monitoring arrangement. More simplified manners of doing the same thing may involve such casual approaches as using strips of markable adhesive tape that are adhered adjacent the location of the switch control and monitoring means of the switch in question, and marked with crayon or ink.

A principal object of this invention is to provide a control panel arrangement of equipment of this type that includes an in field markable legend sheet therefor for both identifying the controlling switches or other components involved and their functions, and organization of the control panel circuit board, legend sheet and associated parts to lay out the control panel in columnar modular form, in which individual modules, which include the switch identification, location to actuate same manually, the switch observation light emitting device, such as a glow bulb, and viewing window therefor, are spaced apart to accommodate application to the legend sheet, adjacent the control and monitoring means of the switch or other component involved, a label that may be in field marked at the time of the control panel assembly as needed to identify the control involved.

Another important object of the invention is to provide a label assembly coordinated to the organization of the aforementioned legend sheet, that includes a carrier sheet and label sheeting removably adhered thereto, both precut to define the individual labels and special handling components associated with same, and hold same assembled for typing or other application of control information thereto, in the order that the control components will be mounted in the control panel, and yet permit easy removal of the individual labels from the carrier sheet and accurate and neat application of the labels to the legend sheet.

Another important object of the invention is to provide a pre-cut label assembly of the type indicated such that the individual labels at each of their ends include a throw-away tab portion that for removal of the label from its carrier and application of the label to the legend sheet, remains adhered to the label to serve as handling tabs, but after the label has been properly centered on the label sheet, are removed from the label ends with the label ends may be smoothed flat in place on the legend sheet in centered relation hereto.

Other objects of the invention are to provide a control panel arrangement of simplified and organized manner that includes an in field markable legend sheet that may have the control component function identification indicia applied thereto after assembly of the control system and prior to assembly of the control panel, to provide a system of labeling control panel legends for programmable controllers wherein the legend sheet and circuitry of the control panel are organized or laid out on a columnar modular group form, including spacing between the individual modular groups for receiving function identification indicia bearing labels, to provide a label assembly coordinated to the organization of the legend sheet, and pre-cut for in field marking of the labels in the assembled relation of the label assembly, and facile handling of the individual labels for manually separating same from the label assembly carrier and application of same to the legend sheet in an accurate neat manner.

The invention is disclosed in association with a control panel arrangement of the membrane or keyboard switch type, as membrane switch arrangements are now commonly employed as part of programmable and other controller equipment. However, this is primarily for illustrative purposes only, since, as will be appreciated by those skilled in the art, the basic arrangement involved is really applicable to control arrangements involving other types of switches.

In accordance with the control panel organization aspect of the invention, a membrane switch control panel system is provided including a circuit board having circuitry integrating a predetermined number of control input and output switches including, for each controlling switch, a pair of contacts on one side of the board to be manually closed, membrane switch fashion, and a glow bulb or the like connected for illumination when the circuit involved is energized through an aperture in the board, a membrane sheet of flexible non-metallic material, such as Mylar polyester, a polycarbonate, or the like, coextensive with and overlying said one side of the circuit board, with one side of the membrane sheet engaging the said adjacent board side, and with the membrane sheet being formed to define apertures aligned with each set of switch contact pairs and having secured over each of its said apertures on the other side of the membrane sheet a planar electrically conductive switch contact closing member of film thickness dimensions for manual (by touch) closing of the aperture exposed switch contacts. Next to the membrane sheet is a legend sheet formed from a flexible non-metallic material such as Mylar that is coextensive with and overlies the side of the membrane sheet bearing the switch contact closing members.

The legend sheet bears switch number indicia imprinted on for the respective controlling switches in alignment with the contacts of that switch that are to be closed by the touch system employed, and the indicated switch number indicia also serves as the switch location indicia.

This basic assembly is secured to the control panel itself which is ordinarily in the form of a rigid metal sheet that is apertured to define the window opening for viewing the legend sheet.

In accordance with the improvements of this invention, the switching system involved in the control panel arrangement contemplates that the circuit board circuitry, the membrane sheet apertures and switch contact closing members thereof, and the legend sheet switch location indicia for all of the respective control switches are arranged in modular, columnarly organized, spaced apart form in which each switch module comprises a set of circuit switch contacts to be closed and opened (to control a particular circuit), a membrane aperture and switch contact closing member for the indicated set of circuit switch contacts, a legend sheet switch location indicia indicating the switch involved. Each of such sets provides a keyboard type micromotion switch, with it being contemplated that each such module may include, for each switch, the aforementioned glow bulb or its equivalent together with a viewing aperture therefore formed in the membrane sheet and a viewing window therefor provided in the legend sheet. Further, each such module may include several of such sets in side by side relation in row form.

The indicated modules are consecutively spaced in columnar form across the length of the control panel with the modules being in substantial parallel relation to define between same a switch function identification indicia receiving zone adjacent the respective modules, which zones as located on the legend sheet are to have applied thereto the label affixed to the legend sheet on the side of same that faces away from the membrane sheet with the respective labels to bear in field applied functional identification indicia of the switch sets forming an adjacent module.

Further in accordance with the invention, a label assembly is provided that is especially adapted for in field application of the switch identification indicia to the control panel legend sheet. The label assembly comprises a label carrier sheet having a suitable release facing to which is releasably adhered an adhesive backed label forming sheet that may be formed from vinyl, polyester, a suitable paper base, or the like. The label assembly is pre-cut in such a manner that while the assembly remains assembled for use in applying the switch identification indicia thereto, the individual labels are preformed in a special shaping to have separated end tabs at either end of same that are held adhered thereto when the label is initially freed from its carrier by separate segments of the carrier that are also preformed for this purpose.

With regard to the individual labels, the precutting of the label forming sheet is to provide a plurality of quadrilaterally shaped labels in columnar arrangement each proportioned to have a blank facing having an area approximating the indicated legend sheet blank areas, with each label having at either end of same a terminal end portion and an associated but severed tab section that also has a width approximating that of the respective labels. The label carrier sheet, on the other hand, is segmented to define at each label end a joiner section that is fully severed from the carrier sheet.

The indicated joiner sections are aligned with the respective label ends to overlap the respective label ends and the terminal tab section associated therewith, but for each label, the label carrier joiner sections are fully severed therefrom and also extend short of the mid portion of the label.

The label forming sheet is also segmented to define between each part of same that is to form a legend label a label spacing section that has a length approximating the length of the respective labels.

The label forming sheet also has imprinted on same alignment indicia, which for the respective labels comprises a vertical line formed in each label tab section that is spaced apart across the length of the label a distance equivalent to vertical lines defined by an indexing marginal border delineated on the legend sheet. In addition, the individual label spacing sections are imprinted with a dividing line indicating the location of the switch identification indicia to be applied to the label in accordance with the location of the switch set to be covered thereby. The label tab sections are also imprinted with guide lines for typing or printing the indicia in a selected number of lines, such as two of three lines.

It is further a feature of the invention that the control panel arrangements and label assemblies will be coordinated in terms of the number of switch identification areas that will be available on the legend sheet and a corresponding number of labels to be provided by the label assembly therefor. Optionally, the label assembly can include one or more additional labels to acommodate the always possible indicia applying errors that might require the discarding of a particular label.

When the controller apparatus involved, especially its switching control, have been assembled, the correlation between the separate switches and circuiting controlled thereby is known, and in most instances this can only be known when the apparatus involved is being assembled in the field. The worker having this information in hand can take a carrier assembly arranged in accordance with the invention as herein disclosed, and apply the assembly to a typewriter or the like, while the label assembly remains assembled, and type onto the individual labels the switch function identification indicia involved that is to identify the particular switches that the respective labels are to be associated with. Alternately the switch function identification indicia involved may be applied to the labels by hand, or by employing suitably sized "rub on" or transfer lettering.

After all the labels have been so marked in accordance with the switching components employed in a particular installation, as part of the assembly of the control panel, individual labels are separated from the label carrier sheet and applied to the legend sheet areas provided for same, by using convenient finger manipulations of the labels.

Thus, each label may be removed from the carrier sheet by grasping the label tag segments at each end of the label and pulling the label free from the carrier, which exposes an uncovered adhesive bearing portion of the label, The worker then holds the label tab ends in either hand, as between a thumb and forefinger, and aligns the tab section alignment lines with the corresponding centering lines of the legend sheet. When this is done, the label is placed against the legend sheet and the center portion of same smoothed down to firmly adhere to the legend sheet. The severed carrier sections that the individual labels each carry now may be removed from the label terminal ends to take with them the severed tab sections, which now may be disposed of. The label ends are then smoothed into place against the legend sheet using finger pressure.

When all of the labels to be employed on a particular legend sheet have been applied thereto, the components of the control panel, including the circuit board, the membrane sheet, the legend sheet, and a transparent cover sheet, which may be formed from a transparent plastic material such as Mylar, and is applied over the legend sheet to protect the labels, are assembled in superposed relation and appropriate fasteners applied between the circuit board corners, through the control panel sheets described into fastened relation with the control panel metal cover plate.

Other objects, uses, and advantages will be obvious or become apparent from a description of the accompanying drawings in which like reference numerals indicate like parts throughout the several views.

In the drawings:

FIG. 1 is a diagrammatic exploded perspective view illustrating the principal components of a control panel arrangement in accordance with the present invention;

FIG. 2 is a fragmental plan view of the control panel arrangement as assembled, with parts broken away to expose underlying parts;

FIG. 3 is a top plan view of the legend sheet of the control panel arrangement of the present invention;

Figure 4:
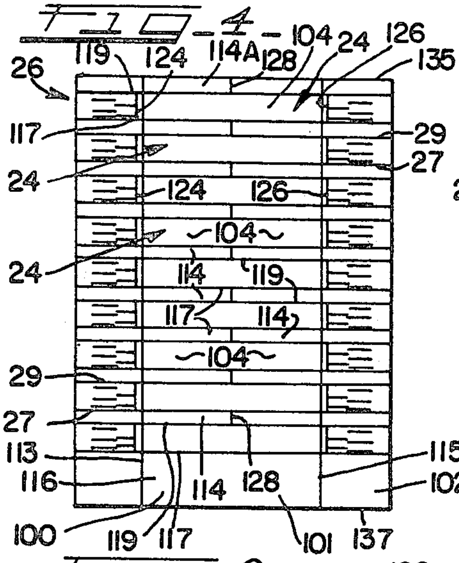
FIG. 4 is a top plan view of a label assembly arranged in accordance with the present invention.

However, it is to be distinctly understood that the specific drawing illustrations provided are supplied primarily to comply with the requirements of the Patent Laws, and that the invention is susceptible of modifications and variations that will be obvious to those skilled in the art, which are intended to be covered by the dependent claims.

Reference numeral 10 of FIG. 1 generally indicates a diagrammatically illustrated control panel arrangement of the membrane or keyboard switch type, which comprises conventional circuit board 12, membrane sheet 14, legend sheet 16, cover sheet 18, and the control panel housing or mounting plate 20 to which the assembled components of the control panel arrangement are secured, as by employing suitable screw and nut assemblies 22.

The invention contemplates that the legend sheet 16 will have applied thereto labels 24 that are available for use in connection with the control panel arrangement 10, and specifically when same is in course of assembly, as part of the label assembly 26 that is illustrated in FIGS. 4–7, with the individual labels 24 being applied to the legend sheet 16 in the manner indicated in FIGS. 8–11.

The circuit board 12 is entirely conventional in nature and is shown and arranged for membrane or keyboard, touch sensitive, switch use. The board 12 comprises a suitable substrate, formed, for instance, from suitable molded thermoset phenolic base or epoxy fiberglass base type materials, or the like. Formed on the circuit board 12 is the usual electrically conductive leads or traces 30 that are usually in the form of copper or the like electrically conductive metal applied to the board using one of a number of available circuit board manufacturing procedures.

The particular circuit board illustrated being designed for membrane switch type use has its electrical circuiting arranged to define a number of switch contact sets 32, each comprising contact components 34 and 36 (see FIG. 2) that are to be closed, membrane switch fashion, to energize an electric closed circuit that the switch 32 in question closes. The board 12 in question has electrical circuiting formed on both sides of same and the leads extend to the end 38 of the board for connection to other leads of the circuiting that the circuit board 12 is associated with in any conventional fashion. The back side of the board 12 for each switch 12 is equipped with a suitable light emitting device, such as the diagrammatically illustrated glow bulb 35 for each switch 32 that is electrically connected as between contacts 37 on the back side 39 of the board 12 (which contacts 37 are aligned with small board holes 31) to glow or emit light so as to be visible through board apertures 43 when the circuit the switch 32 controls is electrically energized. Bulb 35 is intended to represent any suitable device of this character, the function of which can be served by a conventional form of light emitting diode (LED); the term "glow bulb" as used in this disclosure means devices of this type and their equivalents.

The membrane sheet 14 is formed from Mylar polyester or the like of a suitable thickness, and for each switch 32, it is formed with an aperture 40 to be aligned with the contact components 34 and 36 thereof and an aperture 42 to be aligned with the glow bulb 35 with which the respective switches 32 are associated. Membrane sheets of the type indicated are also equipped with an electrically conductive switch closing member that is to span the individual apertures 40. Such a member is conveniently made from a strip of stainless steel 302 of film proportions, and in the form shown in FIG. 1, the membrane sheet 14 has two such members 48 bonded thereto and positioned to overlie the membrane sheet switch exposing apertures 40.

The legend sheet 16 is formed from transparent Mylar polyester or the like and is of special significance that will be described in detail later. At this point, it is appropriate to note that the legend sheet 16 bears, for each switch 32, an identification indicia 50, which as indicated in FIGS. 1 and 2, involves an assigned number of the switch involved, and a viewing window 52 through which the glow bulb of the respective switches 32 may be observed.

Overlying the legend sheet 16 is cover sheet 18, that also may be formed from transparent Mylar polyester or the like.

In the form shown, the board 12, the membrane sheet 14, the legend sheet 16, and the cover sheet 18 are of substantially identical quadrilateral configuration, rectangular in the form illustrated, and each is formed with openings 56 at their respective corners and midlength portions to receive the fastener devices 22 for securing the control panel arrangement in place on mounting or support plate 20, one of which is shown in FIG. 1 in the form of a screw and nut device.

In accordance with this invention, control panel arrangement 10 organizes the locations of the respective switches, their glow bulbs, and their glow bulb viewing apertures and windows (as the case may be) in modular form, in which the individual modules 60 are columarily arranged in spaced apart relation across the length of the control panel. Thus, each module 60 comprises in the form illustrated, and in the assembled relation of the control panel arrangement, a circuit board switch 32 and its associated glow bulb 35 at its requisite aperture 43, the apertures 40 and 42 of the membrane sheet 14 that are respectively aligned therewith, and the identification indicia 50 and viewing window 52 of the legend sheet that are aligned therewith. In the specific form shown, each module is of bipartite form and includes two of the switches 32 (and the associated glow bulb and viewing apertures 37) and the membrane sheet and legend sheet component parts just mentioned associated therewith, in a row across the width of the control panel, though obviously each module could include additional such sets, depending upon the specific design of the control panel.

Further in accordance with the invention, the individual modules 60 are spaced apart along the length of the control panel to provide a blank space 62 therebetween, on the front side 64 of the legend sheet, to receive the respective labels 24.

Figure 12:
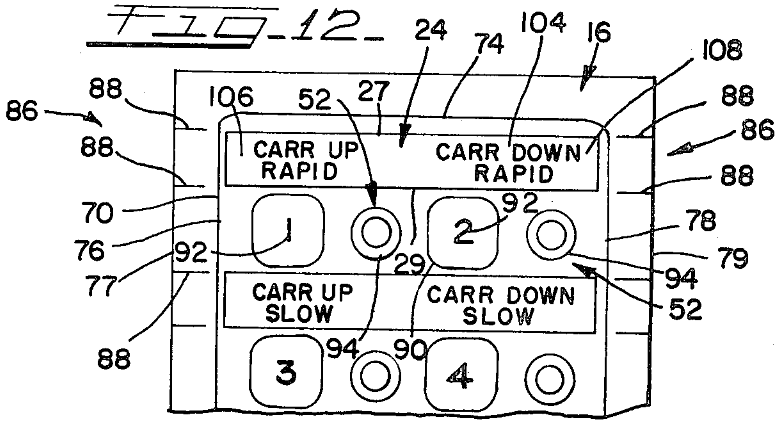
FIG. 12 is a view similar to FIGS. 10 and 11, but illustrating the label as fully applied to the legend sheet.

As has been described hereinbefore, the individual labels 24 are to bear "in field" applied identification indicia relative to the switches they are applicable to. In the form shown, each label 24 is proportioned to bear the functional identification indicia needed with regard to the two switches with which each module 60 is equipped, as indicated in FIGS. 2 and 12, which also indicate that the labels 24 are, in the form illustrated, applied above the module 60 that contain the switches that are to have functional identification indicia applied to the label 24 employed with reference to same (the labels 24 are to be located on the legend sheet 16 where indicated in dashed lines in FIG. 3).

The legend sheet 16 is also formed to delineate a quadrilateral border or marginal line 70 comprising rectilinear sides 72 and 74 that parallel the respective modules 60, and recilinear elongate sides 76 and 78 which extend normally of the respective module 60. The quadrilateral marginal line 70 has a special locating and centering function for facilitating the application of the individual labels 24 thereto, as will be described hereinafter.

The arrangement of the control panel 10 to define the modules 60 permits the use of two of the switch closing members 48 in elongate membrane sheet spanning form, as the switch exposing apertures 40 of membrane sheet 14 will be aligned in two rows that extend longitudinally of the circuit board and corresponding control panel arrangement, thereby avoiding the need to use a separate switch closing member at each aperture 40.

The legend sheet 16, and specifically its delineations and indicia markings that are illustrated in FIGS. 1 and 3, is formed by cutting the sheet 16 to the size indicated in the drawings from a stock of Mylar polyester or the like that is transparent in nature. The sheet 16 then has the switch identification indicia 50 and the viewing windows 52, for each switch 32 that is to form a part of the switch panel arrangement 10 delineated on same as well as marginal line 70, for instance, on the back side 65 of same. This can be readily done by employing a suitable silk screening procedure. At the same time, any product name or trademarking is formed on the back side 65 of the sheet 16, where indicated by reference numeral 80. In addition, the back side 65 of sheet 16 also has formed along its longitudinal edges 82 and 84 exteriorly of the marginal line sides 76 and 78, spaced pairs 86 of label centering indicia 88 for properly aligning the individual labels 24 with the respective label receiving spaces 62. The lining indicia 88 are in the form of indexing lines that are spaced apart, in each set 86, the width of the label 14.

It is to be noted that the switch identification indicia 50 in the form shown conveniently comprises a quadrilateral marginal line 90 within which is centered an arabic number or numeral 92. The associated viewing window 52 is defined by ring 94 that encircles a light transmitting area which may be uncoated and thus is a transparent area of the sheet 16; where an LED is employed as bulb 35, window 52 should be colored appropriately to pass the light emitted thereby.

The rings 94, the marginal lines 90 and their numerals 92, the marginal line 70, the indexing indicia lines 88, and the trademark and trade name indicia 80 are all formed on legend sheet 16 by opaque material such as a suitable ink, as indicated, a suitable silk screening procedure will be satisfactory for this purpose.

Thereafter, the back side of the legend sheet 60, except for the viewing windows defined by the rings 94, are covered with a contrasting but opaque color, such as yellow, employing, again, a suitable silk screening procedure. Preferably the color employed for this purpose and the color of labels 24 is the same. The result at this stage is the legend sheet 16 substantially as it appears in FIG. 3 (it being understood that the yellow color mentioned above is omitted to simplify the drawing).

While the delineations, indicia, and coloring indicated are described as applied to the back side 65 of legend sheet 16, they may be applied to the front side 64, which would involve a reverse order of printing.

It will thus be seen that legend sheets 16 are arranged in a generic manner to follow the basic switch modular organization of the control panel arrangement 10, with the switch number indicia applied to the sheet 16 being readily applicable to any contemplated panel arrangement 10 that has no more switches than exceeds the number of the switches given on the legend sheet 16, which for the illustrated embodiment is sixteen. The individual legend sheets 16 that are formed as indicated thus have the label receiving places 62 blank for application of the individual labels from a label assembly 26.

When a particular programmable controller arrangement is installed in association with a specific assembly industrial processing equipment, the function of the individual switches involved in the individual controller system will only then be known. In accordance with this invention, prior to the assembly of the control panel arrangement 10, after the functioning of the individual switches involved in circuit board 12 is known, the panel sheet 16 has the individual labels 14 applied thereto to give, for each switch involved, this needed functional indicia formation. The label assembly 26 is arranged so that when this information is known, the assembly 26 may, for instance, be applied to a typewriter or the like as a whole, and the needed information applied to the individual labels consecutively, until all of the labels involved are needed for a particular installation are so marked, all without separating the labels 24 from the assembly 26.

The label assembly 26 (see FIGS. 4–8) comprises a label sheet 100 and a label carrier sheet 102. Label sheet 100 as a whole may be formed from, for instance, a suitable vinyl, polyester, or paper based, or other materials commonly employed for making label substrates, and have an appropriate pressure sensitive adhesive coating suitable for labels formed from this material, such as a suitable acrylic adhesive of any conventional type.

The carrier sheet 102 may be a suitable paper based substrate that is coated or impregnated with a suitable release agent, such as silicone, or silicone rubber, for releasably receiving the adhesive coated side of the label sheet, all in a conventional manner.

Materials suitable for forming the label components of label assembly 26 are involved in the pressure sensitive labels made and sold by Fassion Division of Avery International Co., Painesville, Ohio, from which materials label components may be selected to form label sheet 100 and carrier sheet 102, as the basic composite label sheeting from which assembly 26 is formed in accordance with the present invention.

The label assembly 26 is formed by taking appropriate lengths of an opposite blank sheet 100 adhered to a blank carrier sheet 102, which product is available commercially in either sheets or rolls. When the composite label sheeting is cut to the appropriate width for application to legend sheets 16, the resulting composite label sheeting is run through a suitable die cutting machine such as the Mark Andy 820 System offered by the Mark Andy firm of St. Louis, Mo. The purpose is to sever the label forming sheet 100 and the label carrier 102 as will now be described for each label assembly 26 formed, and in such a manner that while the individual labels 24 are formed, the assembly 26 will remain assembled until the labels 24 are deliberately removed therefrom by the worker. The length of composite label sheeting being so treated will also be scored between consecutive label assemblies 26 so that they may be separated as needed along such score lines.

Figure 5:
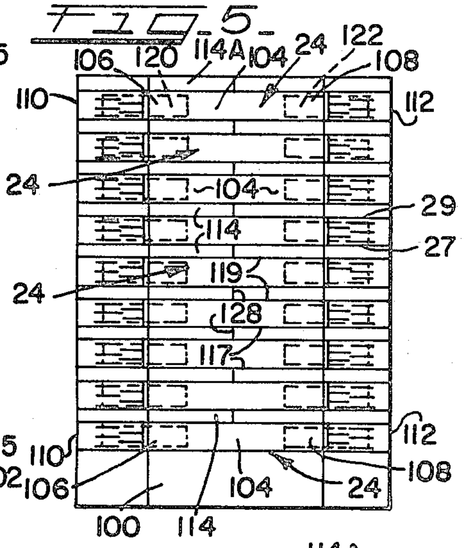
FIG. 5 is a top plan view of the label sheet as it would appear if totally removed in assembled relation from the backing sheet, with the severed backing sheet sections that join the label tab sections to the respective label terminal ends being shown in dashed lines.
Figure 6:
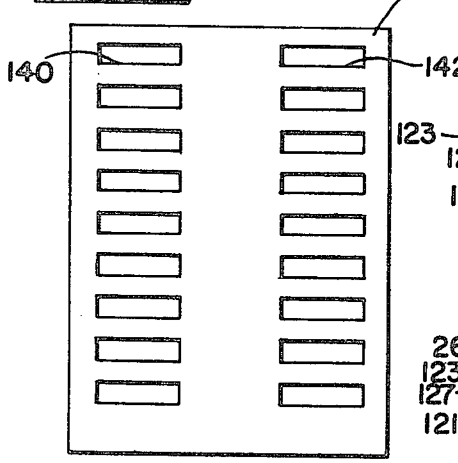
FIG. 6 is a plan view of the label carrier sheet as it would appear after the label sheet as shown in FIG. 5 is removed therefrom.

The label sheet 100 is shown in FIGS. 4 and 5 in the form it takes in a completed label assembly 26 (that has been separated from the indicated length of composite label sheeting that is formed as indicated to shape the indicated series connected label assemblies 26).

Figure 7:
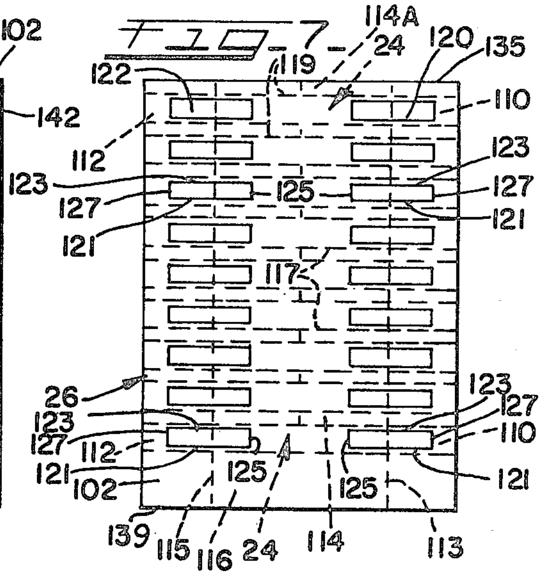
FIG. 7 is a bottom back plan view of the label assembly as shown in FIG. 4.

FIG. 5 shows the preformed label sheet 100 as it would appear from the front side of same if removed as a whole from the carrier sheet 102, with portions of the carrier sheet that are to temporarily adhere to same, in accordance with this invention, being shown in dashed lines. In the showing of FIG. 7, the back side of carrier sheet 102 is shown in plan and the label sheet 100 and the severing lines formed in same are shown in dashed lines.

Figure 10:
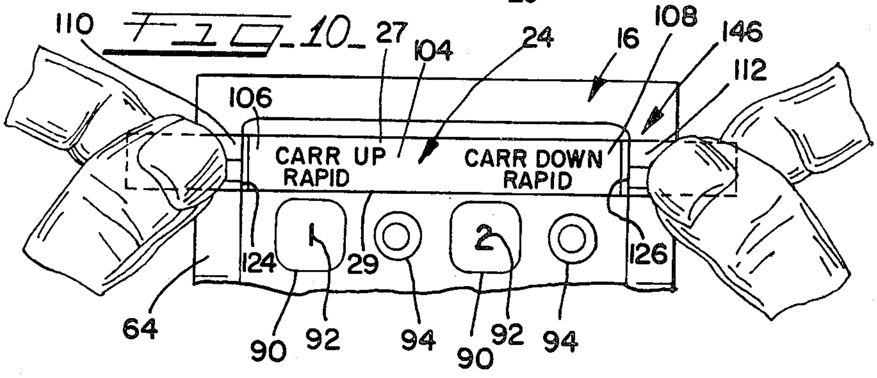
FIG. 10 is a view similar to that of FIG. 8, but illustrating the removed label in the course of being applied to the control panel legend sheet of FIG. 3 in accordance with the practice of the invention.
Figure 11:
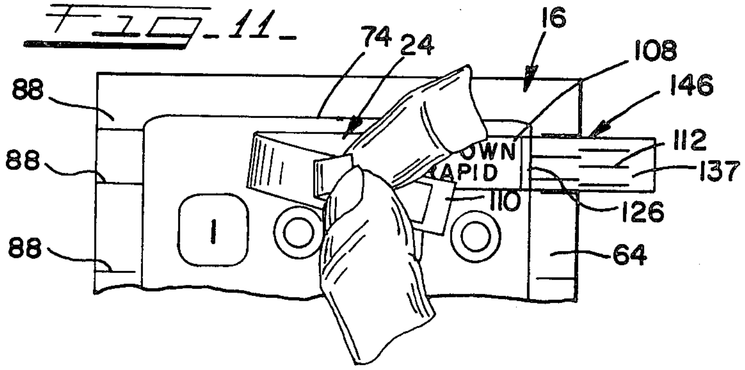
FIG. 11 is similar to FIG. 10, but illustrates the procedure of moving the label tag segments in accordance with the invention.

The label sheet 100 is thus precut or subdivided to form severing cuts illustrated by severing lines 113, 115, 117 and 119, that define, among other components, the individual labels 24, which as indicated in FIGS. 10 and 12 are of quadrilateral configuration (rectangular in the illustrated embodiment) defining an outwardly facing markable or typewriteable blank facing 104 to which the switch functional informational indicia is to be applied. The individual labels 24 also each have terminal end portions 106 and 108 at either end of same.

Figure 8:
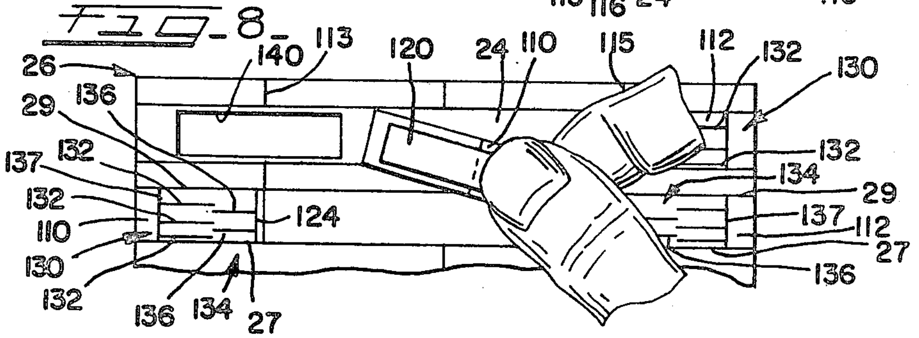
FIG. 8 is a fragmental top plan view of the label assembly shown in FIG. 4, but on an enlarged scale and illustrating one of the tab sections of the label assembly being actuated to remove from its carrier sheet the first label, of the label assembly, in accordance with the practice of the invention.
Figure 9:
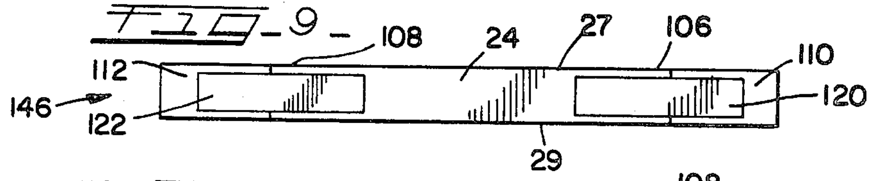
FIG. 9 is a bottom or back plan view of one of the individual removed labels.

The label sheet 100 includes for each label 24, in contiguous relation to the label terminal end 106 a tab section 110, and contiguous to the label end 108, a tab section 112. The labels 24 have a length that is somewhat less but approximates the distance between the sides 76 and 78 of the legend sheet marginal line 70, and is defined by severing lines 113 and 115 that run the length of assembly 26. The labels 24 have a width equivalent to the distance between the legend sheet alignment lines 88 of the respective indicia sets 86 and is defined by transverse severing lines 117 and 119. The tab sections 110 and 112 have a width that is the same as the width of the labels 24 and that is formed by the same severing lines 117 and 119 forming the individual labels 24, and in the form shown, the tab sections 110 and 112 each have a length that exceeds the distance between the marginal line side 76 and the adjacent side edge 77 of the sheet 16, in the case of tab sections 110, and the marginal line side 78 and the adjacent legend sheet side edge 79 in the case of tab sections 112: the actual length of the tab sections 110 and 112 employed need be no more than to facilitate the handling that is described hereinafter and that is illustrated in FIGS. 8–11. In any event, the tab sections 110 and 112 as adhered to a label 24 extend lengthwise of same well beyond the distance between the legend sheet marginal line sides 76 and 78, as indicated in FIGS. 8–10.

The label sheet 100 also includes a severed spacing section 114 between the adjacent labels 24, as well as a top or header spacing section 114A at the upper end of the label assembly 26, all formed by the respective severing lines 117 and 119.

At the lower end of the label sheet 100, a severed base section 116 is provided which may be employed to serve as a masking cover for the legend sheet space 81 in the event that masking of the product name and trademark indicia that may be provided in the space 81 (in the form the legend sheet 16 is printed up) is desired to be masked.

It is to be understood that the labels 24, the tab sections 110 and 112, the spacing sections 114, the header section 114A, and the base section 116 are all severed sections of the label sheet 100 (severed along severing cuts shown as severing lines 113, 115, 117 and 119, which sever sheet 100 but not sheet 102), which are held together by adherence to the carrier sheet 102.

The carrier sheet 102 is precut during the formation of the label assembly 26 to form a pair of joiner sections 120 and 122 for each label 24. As is indicated in FIGS. 5, 7 and and 9, the joiner section 120 overlaps the label terminal and 106 and its tab section 110, while the joiner section 122 overlaps the label terminal end 106 and its tab section 112. The joiner sections 120 and 122 are of quadrilateral configuration (rectangular in the illustrated embodiment), and are of equal dimension in width, which dimension is less than the width dimension of the respective labels 24 and their tab sections 110 and 112, as indicated in FIGS. 5, 7, 8 and 9. Joiner sections 120 and 122 are formed physically by severing cut illustrated by severing lines 121, 123, 125, and 127 of FIG. 7.

A further processing involved to provide the label assembly 26 involves imprinting on the outwardly facing surface 101 of the label sheet the locating indicia that is best illustrated in FIGS. 4 and 8.

This includes the label sheet 100 being delineated to define across the width of the label tab sections 110 centering lines 124 that are aligned longitudinally of the assembly 26, and centering lines 126 across the width of the tab sections 112 which are also aligned longitudinally of the label assembly 26. The lines 124 are spaced across the width of the label assembly 26 from the lines 126 a distance equalling the distance between legend sheet marginal line sides 76 and 78 (see FIG. 10).

In addition, the spacing sections 114 and the header section 114A are each delineated to have a centering line 128 located at the longitudinal central axis or center line of the label assembly 26.

Further, the tab sections 110 are delineated to define a first set 130 (see FIG. 8) of indicia forming guidelines 132, and a second set 134 of indicia forming guide lines 136. Similarly, the label tab sections 112 are delineated to define a similar set 130 of indicia guide lines 132 and a second set 134 of indicia guide lines 136. As will be observed from FIGS. 4, 5 and 8, indicia guide lines 132 are three in number and are aligned crosswise of the label assembly 26, while the indicia guide lines 136 are two in number, and are aligned crosswise of the label assembly 26. Guide lines 132 and 136 on either end of labels 24 extend from upright base lines 137 in the illustrated embodiment.

The delineations represented by centering lines 124, 126 and 128, and the guide lines 132 and 136 are formed on the face 102 of label sheet 100 by a suitable printing procedure, preferably before the indicated severing of the label sheets 100 and 102 has been effected. Following conventional procedures of precutting the label sheets 100 and 102, as by employing the aforementioned Mark Andy 820 System, the label assemblies 26 are formed in the indicated multiple unit consecutively located manner on a continuous strip of label material comprising commercially available labeling sheeting adhered to a carrier sheeting, cut down to appropriate width size for processing in accordance with the invention. The score lines (not shown) for separating individual label assemblies 26 are formed along the upper and lower edges 135 and 139 of the respective label assemblies 26 and correspond thereto.

In using label assembly 26, when it has been determined what functions the switches involved in a particular control assembly will have, these are itemized for the assembly of switches employed and reduced to appropriate terminology to be applied to the labels 24 of a particular label assembly 26. Thus, it will then be determined what function switches 1 through the number of the switches the controller assembly is to have (up to 16 in the illustrated embodiment) which results in the determination of the function identification indicia to be applied to the respective labels 14.

A label assembly 26 is then taken as a whole, and the labels consecutively marked accordingly, on their respective blank facings 104. Thus, for the top label 24, which is to be applied to the location indicated in FIG. 12 above the first switch module 60, the functional indicia involved for switch No. 1 would be applied to the left hand side of the top label 24, while the corresponding indicia for switch No. 2 of the module 60 would be applied to the right hand side of the label 24, with the centering lines 128 above and below the top label 24 indicating to the operator the necessary spacing that is to be made between the indicia employed for the indicated switches No. 1 and 2.

Similarly, the next label 24 of the label assembly 26 is marked in a similar manner for the switches 3 and 4 involved in the second switch module 60, with the second label 24 to be applied in the blank space 62 between the first and second switch modules.

For purposes of illustration, it is assumed that the circuits that may be actuated by switches Nos. 1–4, respectively, will effect movement of a processing equipment carriage component (not shown) upwardly or downwardly, rapidly or slowly. FIGS. 10 and 12 show the corresponding information applied to the labels 24 that are to be applicable to switches Nos. 1–4, as contemplated by this invention.

This marking of the labels 24 continues until all of the switches that will be employed in control panel arrangement 10 are taken care of. It is intended, as indicated, that the labels 24 of an assembly 26 remain in place on carrier 102 until all marking of the labels 24 of a particular assembly 26 intended for a particular control panel arrangement 10 is completed. As has also been indicated, the function indicia involved can be applied to the labels 24 while still a part of assembly 26 by typing, handing, printing, using rub on transfer letters, or the like.

The blank section 116 of assembly 26 is available for similar application of indicia thereto to provide other information that may be desirable or necessary other than the product name and brand name indicia that would normally appear in the space 81 of the legend sheet. In any event, it will be apparent that the individual labels 24 and blank section 116, as adhered to carrier sheet 102 and thus still part of label assembly 26, are much more readily marked with the indicated functional indicia than if separated from assembly 26. Assembly 26 as a whole may conveniently be applied to a typewriter for this purpose, or laid on a firm flat supporting surface for manual printing of the indicia, applying rub on transfer lettering, etc. The label assemblies 26 may be provided with one or more extra labels 24 and associated parts, for a particular legend sheet 16, to allow for label spoilage.

Assuming that the application of the indicated indicia to the label assembly 26 has been completed, the next step is to apply the individual labels 24 to the legend sheet 16.

This may be done as diagrammatically illustrated in FIGS. 8–11 for the top label 24.

This involves first grasping either the label tab section 110 or the tab section 112 (the tab section 110 is shown grasped in FIG. 8) to separate the tab section involved from the label carrier 102. As the pulling action involved proceeds, the joiner section (for instance section 120) that joins the tab section being pulled to a label terminal end (for instance end 106) is drawn out of the label carrier sheet 102 leaving quadrilateral a void (for instance void 140) that complements the rectangular shape of the joiner section. The entire label 24 may be freed from the carrier section 102 by continuing to draw the label 24 to the right of FIG. 8 until the other tab section (for instance section 112) is also freed from the carrier section, this action also drawing with it the second joiner section (for instance section 122) that leaves a void (for instance void 142) in the carrier sheet 102.

FIG. 9 is a plan view of a label 24 that has been so separated from carrier sheet 102, taken from its back side, showing the label 2 together with its associated tab sections 110 and 112 and the joiner sections 120 and 122, which thus form a label handling arrangement or subassembly 146, for applying the individual labels 24 to the legend sheet 16. Of course, the subassembly may be formed by starting at the tab section 112 and pulling the subassembly 146 free from the direction opposite that indicated in FIG. 8.

Processing of the individual label subassemblies 146 to individually apply their labels 24 to the legend sheet spaces 62 may proceed as follows:

With the legend sheet 16 resting on a fixed supporting surface that is preferably horizontal, and with its outwardly facing side 64 facing upwardly, the removed label mounting arrangement or assembly 146 is grasped as indicated in FIG. 10, that is with one tab section 110 grasped between thumb and forefinger of the left hand and the other tab section 112 grasped between the thumb and forefinger of the right hand, and is positioned for proper alignment of the label 24 itself to the blank space 62 defined by the legend sheet to which the label is to be applied, for instance the first blank space 62 of a legend sheet 16. For this purpose, the assembler aligns the centering lines 124 and 126 of the respective tab sections 110 and 112 with the legend sheet marginal line sides 76 and 78, respectively, and in addition the assembler aligns the top and bottom side edges 27 and 29 of the tab sections 110 and 112 with the guide lines 88 of the respective sets 86 for the first label position blank space 62. When the proper alignment has been achieved as indicated, the tab sections 110 and 112 are pressed against the legend sheet, to which they will adhere along their back side portions that extend outwardly of the respective joiner sections 120 and 122 (these areas being adhesively coated portions of the label sheet 100 back or underside). The joiner sections 120 and 122 are made of a narrower width than the labels 24 and their tab sections 110 and 112 for this purpose.

The installer may now run his finger across the length of the label 24 to adhere the middle portion of the adhesive backed side of the label 24 to the legend sheet 16.

The label tab sections 110 and 112 may then be removed and discarded, and to achieve this, the tab sections 110 and 112 are consecutively pulled free of the legend sheet 16 and the joiner sections 120 and 122 separated from the label back side and pulled free of same, whereby the respective tab sections 110 and 112 (which remain adhered to the respective joiner section 120 and 122) will be pulled free of the label 24 and discarded. The terminal ends of the label 24 may now be smoothed back into adherement with the legend sheet 16 to provide the fully applied position of the label that is indicated in FIG. 12.

The remaining labels 24 of the label assembly 20, as needed, are consecutively applied to the legend sheet areas 62 to the extent that switches up to a number 16 switch are to be used in the controller structure involved. The label assembly blank section 116 may also be applied to the space 80 of the legend assembly as and if needed or desired. Of course, the control panel arrangement 10 and associated parts may include any desired number of switches and corresponding modules 60, as needed.

The control panel arrangement 10 including the circuit board 12, membrane sheet 14, the legend sheet 16, and the cover sheet 18, in the order indicated in FIG. 1, are then assembled in an appropriate manner and fasteners applied to the corner openings 56 to secure the assembly to the mounting plate 20, which defines window opening 150 that complements the shape of the legend sheet 16 quadrilateral marginal line 70.

In practice, in assembling the control panel arrangement 10, that is disclosed, the membrane sheet 14 is suitably bonded about its marginal edges to the corresponding marginal edges of the circuit board 12, and the marginal edges of the membrane sheet 114 are suitably bonded to the corresponding marginal edges of the legend sheet 16. The metal strips 48 forming the closing means for the individual switches 32 are also suitably bonded to the membrane sheet 14. It is not necessary that cover sheet 18 be bonded to the legend sheet, and it is necessary that the cover sheet 118 be transparent or essentially so for viewing of the indicia and windowing openings of the legend sheet 16 for mounting plate window aperture 150.

In a modified form of control panel arrangement 10, instead of employing steel strips 48 on membrane sheet 14, a separate sheet formed of Mylar polyester or the like that is transparent is made up for incorporation between sheets 14 and 16, and of the same size and shape, and has imprinted on the back side of same, as by employing silk screening techniques, pads of electrically conductive ink of a type conventionally used on circuit boards, respectively aligned with the respective apertures 40, for severing to close the indicated switch components of each switch by the touch switch system of actuation.

It will therefore be seen that the invention provides a control panel arrangement in which the control panel switches and associated numbering indicia and glow bulbs (or their equivalents) are arranged in modules that extend crosswise of the control panel in a spaced columnar relation. This leaves blank spacing between the individual modules for application thereto of the labels of the Applicant's label assembly. After assembly and assuming the control apparatus involved is connected to a suitable source of electrical energy, finger touching of control panel arrangement 10 at the switch locations indicated by the numerals on the legend sheet will close the switch 32 thereof manually. The glow bulb or its equivalent that is associated with each switch is conventionally not energized (for illumination) directly by the switch itself, but by other circuiting energized by closing the switch components involved. Where the controller system involved is also programmable, the programming tape will actuate the circuits represented by the glow tubes 35 automatically under the control of the tape and associated apparatus involved, permitting the operator to monitor the system by viewing control panel 10. An apparatus suitable for this purpose is disclosed in the Applicant's copending application Ser. No. 963,414, filed Nov. 24, 1978 (the disclosure of which is incorporated herein by this reference).

The Applicant's label assembly permits application to the individual labels to be applied to the control panel legend sheet, in field, the switch functional information indicia that is known only after a control assembly and associated components, as well as assembly of the basic controller apparatus itself, is completed.

The Applicant's label assembly also permits the labels of the label assembly to be individually and consecutively marked while the labels remain part of the label assembly, which as a whole may be handled much more conveniently than the individual labels separately. Thus, the label assembly may be conveniently applied as a whole to a typewriter or the like with the centering guide lines being provided to properly center a switch functional information indicia over the switch module involved in either a two line or a three line format, depending on whether guide lines 132 or 136 are followed. If preferred or desired, the label assembly may alternately be laid on a firm working surface, and the required indicia applied thereto by hand printing or using rub on transfer lettering of any conventional form and sized appropriately for the labels involved.

When marking of the individual labels of the label assembly has been completed, the individual labels may be individually removed from the carrier sheet of the label assembly and applied in neat centered relation to the legend sheet at the appropriate space 62 therefor by utilizing the tab sections 110 and 112 that remain adhered to the individual labels for this purpose. After proper positioning of the label in its indicated space 62, the tab sections 110 and 112 are readily removed and discarded if desired although they could also be left in place without disturbing the functioning of the legend sheet since a sufficient amount of the adhesive covered surface of the label ends 106 and 108 and the tab sections 110 and 112 remains uncovered to keep these parts adhered to the legend sheet. In practice, however, it is preferred that the tab sections 110 and 112 be removed in the manner indicated.

The label assembly 26 is also adapted for general purpose use; label assemblies 26 intended for general purpose use may alternately omit the imprinting of the label sheet 100 that is disclosed herein for simplification purposes.

The foregoing description and the drawings are given merely to explain and illustrate the invention and the invention is not to be limited thereto, except insofar as the appended claims are so limited, since those skilled in the art who have the disclosure before them will be able to make modifications and variations therein without departing from the scope of the invention.

I claim:

1. The method of making a legend sheet for a membrane switch control panel arrangement of generally quadrilateral configuration that includes a circuit board having circuitry integrating a predetermined number of consecutively numbered control input and output switches including for each switch a switch set including a pair of contacts on one side of the board to be manually closed and a bulb connected for illumination when the switch is closed and a viewing aperture in the board, adjacent the set contacts, through which the bulb is visible when so illuminated, a membrane sheet of flexible non-metallic material coextensive with and overlying said one side of the board with one side of same engaging said board side, said membrane sheet being formed to define first apertures aligned with each switch contact pair respectively and having secured over each of its said first apertures on the other side of same a planar electrically conductive switch contact closing member of film thickness dimensions for manual closing of aperture exposed switch contacts, said membrane sheet including second apertures, respectively, aligned with the bulb viewing aperture of the respective switch sets, said legend sheet, which is of flexible non-metallic material and is coextensive with and overlies said other side of membrane sheet with one side of said legend sheet engaging said other side of said membrane sheet, with said legend sheet bearing location indicia for the respective switches by corresponding consecutive number starting at its top and viewing apertures of the respective switch sets, and a rigid mounting sheet to which said circuit board is secured with said membrane sheet and said legend sheet disposed therebetween and with said mounting sheet being apertured to expose for viewing said legend sheet location indicia, with said arrangement including the improvement wherein:

said circuit board switch sets, said membrane sheet first apertures and switch contact closing members thereof, said membrane sheet second apertures, and said legend sheet switch location indicia for the respective switch sets are arranged in like modular form comprising for each module one of the switch sets, a membrane sheet first and second apertures therefor, a membrane sheet contact member for closing the module switch contacts, and legend sheet switch and viewing aperture location indicia for the module switch set, with the switch set of each module being oriented such that in the switch set thereof the contacts and viewing aperture are similarly oriented in side by side spaced apart relation, and with said modules being grouped in parallel, spaced apart rows that extend across the width of said panel arrangement of which each said row has an equal number of said modules, said rows being of substantially uniform height and length, and said modules forming each row being in columnar relation across the height of said panel arrangement, said legend sheet defining for each of said rows and in proximity to same an elongate switch identification indicia receiving zone, with said zones being of substantially uniform length and height, and being substantially coextensive with the respective rows, said method comprising:

after the functions of said switches have become identified, in terms of coordination of switch consecutive number identification and function indicia for each such switch by such consecutive switch numbers, when said circuitry has been assembled, taking a label assembly that comprises a release coated label carrier sheet bearing on said coating thereof a label forming sheet that is segmented to define individual labels of quadrilateral equal size configuration columnarly arranged lengthwise of said label assembly between the ends thereof, applying to said labels in-field, starting at the top end of said carrier sheet, and to consecutive of said labels, lengthwise of said carrier sheet, the switch function indicia, in consecutive order of such switches, for the respective consecutively numbered switches employed in such panel arrangement, while said labels remain adhered to said carrier sheet, and after all such switch function indicia of said panel arrangement have been applied to said consecutive labels of said label assembly, consecutively removing the individual labels bearing said switch function indicia from said label assembly starting at its top end, and adhering same consecutively to corresponding consecutive of said legend sheet zones, starting at the legend sheet top end, to transfer all said labels bearing said in-field applied function indicia to said legend sheet in the consecutive order of said rows, whereby said labels to be in-field applied to said legend sheet have such in-field function indicia applied thereto while remaining a part of such label assembly, after said functions of said switches has been determined by said circuitry having been assembled.

2. The method set forth in claim 1 wherein:

said in-field applied function indicia is applied to said labels by applying said label assembly as a whole to a typewriter and typewriting said function indicia on said labels, respectively, while they are part of said label assembly.

* * * * *